United States Patent
Bähr

[11] Patent Number: 5,906,600
[45] Date of Patent: May 25, 1999

[54] BODY SHOWING ANTIBACTERIAL EFFECT FOR APPLICATION AS A MEDICAL OR SURGICAL AID

[75] Inventor: Judith M. Bähr, Baden-Baden, Germany

[73] Assignee: Gentamed AG, Gersau, Switzerland

[21] Appl. No.: 08/805,620

[22] Filed: Feb. 26, 1997

[30] Foreign Application Priority Data

Feb. 27, 1996 [DE] Germany .................... 196 07 314

[51] Int. Cl.$^6$ ............................... A61M 5/32
[52] U.S. Cl. ................... 604/265; 604/178; 606/72; 606/76
[58] Field of Search ............... 604/265, 178; 606/59, 61, 64, 72, 76; 128/207.16

[56] References Cited

U.S. PATENT DOCUMENTS

| | | | |
|---|---|---|---|
| 4,784,647 | 11/1988 | Gross | 604/178 |
| 5,013,306 | 5/1991 | Solomon et al. | 604/265 |
| 5,242,428 | 9/1993 | Palestraut | 604/265 |
| 5,325,851 | 7/1994 | Reynolds et al. | 128/207.16 |

FOREIGN PATENT DOCUMENTS

| | | | |
|---|---|---|---|
| 1106718 | 8/1981 | Canada | 604/265 |
| 206024 | 12/1986 | European Pat. Off. | 604/265 |

*Primary Examiner*—Michael Buiz
*Assistant Examiner*—Julian W. Woo
*Attorney, Agent, or Firm*—Max Fogiel

[57] ABSTRACT

The invention proposes a body showing an antibacterial effect for application as a medical or surgical aid, wherein the body is designed as a flexible synthetic-material hose (8) that is provided with an antibacterially-acting coating, and the hose (8) is provided with a slit (8a) over its entire length.

18 Claims, 1 Drawing Sheet

BODY SHOWING ANTIBACTERIAL EFFECT FOR APPLICATION AS A MEDICAL OR SURGICAL AID

BACKGROUND OF THE INVENTION

The invention concerns a body of synthetic material showing an antibacterial effect, for application as a medical or surgical aid.

It is known that antibiotics, in particular gentamicin, are released from synthetic materials based on polymethacrylates and/or polyacrylates in a protracted manner. In this, an initial steep concentration drop, indicating the release from the outermost layers of the synthetic material, is followed by an almost constant release that slowly diminishes over a long period of time. These antibiotic-containing synthetic materials have been employed, for example, as bone cement for the attachment of endoprostheses, for example total-hip endoprostheses, or in the replacement of infected endoprostheses. For the fighting or prevention of infection, here the antibiotics were added before the complete polymerisation of the synthetic material. From DE-PS 23 20 373 is known in addition an antibiotic-containing aid in the form of a sphere, which aid contains a synthetic material, the antibiotic being distributed uniformly in the synthetic material. The spheres have a diameter of 1 to 20 mm and are preferably connected to one another by means of threads or wires. This aid serves, for example, for the filling of osteomyelitic cavities for the creation of an aseptic transplant bed, and so on. Further, from EP 0 236 468 B1 is known a pin for insertion into a borehole located in a bone, which pin consists of a carrier of synthetic material based on polymethacrylate and/or polyacrylate or similar material, and shows the antibiotic, preferably gentamicin, in uniform distribution, wherein the carrier has a cylindrical form and its inner space serves for the taking up of a bone nail or a bone screw of an external fixing device.

In addition, from DE 36 27 487 A1 is known a vessel prosthesis in the form of a hose, wherein the hose consists essentially of synthetic material and its end region to be sewn up or clamped is formed as a storage space for an antibiotic for the lessening of the risk of infection. The hose is sewn up with the blood vessels to be joined in each case and is thereby effective, for example, as a bypass. A similar vessel prosthesis is known from U.S. Pat. No. 3,425,814. There the inner wall of the hose shows an antibiotic.

From EP 0 693 300 A2 is known a catheter with several longitudinal slits arranged next to one another and extending over a short length.

With a stopping up of the distal outlet end of the catheter by means of a stopper or the like, the infusion fluid exits through the longitudinal slits by means of the pressure deformation of the catheter in this region, and by means of the deformation of the distal end of the catheter the stopper is loosened, whereupon the longitudinal slits again close.

In all surgical situations in which the skin is pierced, cut into, or in some other way injured, the risk of microorganisms penetrating the body tissue and causing a local or systemic infection is greatly increased. The wound that exists over a longer period of time, for example in consequence of postoperative vacuum drainage, external fixing nails in orthopedics, and so on, represents a considerable infection risk for the patients.

SUMMARY OF THE INVENTION

It is the problem of the present invention to develop further a body of synthetic material showing antibacterial effect, for application as a medical or surgical aid, in such a manner that in its simplest configuration it makes possible an effective prophylactic with respect to infections, or an effective local treatment of already existing infections, in the region of the wound.

This problem is solved by means of a body showing antibacterial effect, for application as a medical or surgical aid, in which the body is designed as a flexible synthetic hose that is slit over its entire length, which hose is provided with a coating showing an antibacterial effect.

The configuration of the body as a slit hose makes possible its insertion into the wound region in the simplest manner, the flexibility of the hose allowing it to adapt its form to the geometric conditions present in the region of the wound in each case. The hose configuration permits in particular the application of the hose in conjunction with surgical or orthopedic instruments. It is considered especially advantageous if the flexible hose consists of polyvinylchloride (PVC). Soft PVC is a material with rubber-like properties.

On the basis of the configuration according to the invention of the hose with a slit extending over the entire length, it is not necessary to push this hose axially over an orthopedic fastening element, for example an orthopedic nail or an orthopedic screw or another hose, for example, a drainage hose, but rather, by spreading out in the region of its slit, it can be radially pushed or slipped onto the orthopedic fastening element or the other hose it is to surround. The substantial advantage is to be seen in the fact that the hose showing an antibacterial effect, insofar as it is necessary, can be replaced in the simplest manner by being pulled off radially and replaced by a new hose. With this, it is not necessary that any external fixing possibly provided for the orthopedic fastening element surround by the hose be removed.

It was kept particularly in mind that only hoses of a determinate length or gradations of length are stocked. One therefore gets by with a few pre-determined hose lengths. These hoses having defined lengths are usefully provided with a coating showing an antibacterial effect, while the special slit configuration of the hose makes it possible that this hose be provided in the simplest manner with an antibacterially-acting coating not only on the outside, but also inside and in both end-side regions. The slit configuration of the hose also makes it possible it employ it for different diameters of orthopedic fastening elements or hoses to be surrounded, which considerably reduces the number of hose diameters to be stocked. Thus a hose can find application not only with those fastening elements, or hoses to be surrounded by it, whose outer diameters correspond to the inner diameter of the hose showing an antibacterial effect, with the consequence that the hose slit is closed.

If the orthopedic fastening element or the hose surrounded by the hose has a greater outer diameter, the hose showing the antibacterial effect will nevertheless surround these pieces, although then there is an open slit gap to note, that is, the hose spreads itself by the width of the slit.

In accordance with the purpose the flexible hose is provided with a silver coating. In principle, the body can also be provided with any coating showing an oligodynamic effect that has this antibacterial effect on microorganisms. By this means, local skin and tissue infections can be treated or the hose according to the invention can find application immediately after the wounding of the skin in the sense of a preventive measure.

With the hose according to the invention showing an antibacterial effect, conduits for the delivery of fluids to the body or for the draining of undesired fluids from the body can be provided, in particular in the region of the entrance of the hose into the body. The hose also finds application in conjunction with components that serve for the fixing of the skeleton. The hose has the ability to protect this wound region from microorganisms over a long period of time or, microorganisms being present, to treat it.

Preferably, the hose is held in its longitudinal direction by means of a ring element slid onto it and/or onto a fixing nail or fixing screw, which ring element contacts the skin in the region of the exit of the hose from the body of the patient. In order to ensure a fixing of the ring element in the longitudinal direction of the hose or of the fixing nail/fixing screw, the ring element is slipped onto the hose or the fixing nail/fixing screw by a force fit. Apart from this, there is the possibility of sewing up the hose with the skin in the region of exit from the body of the patient. Provided that the inner diameter of the hose is less than the outer diameter of the fastening elements or of the hose surrounded by the hose showing an antibacterial effect, an element for fixing the hose can be dispensed with if need be, since, owing to the spreading out of the hose in the region of the slit, the hose clamps onto the part surrounded by it.

Additional features of the invention are represented in the dependent claims, the description of the figures, and the figures themselves, it is noted that all individual features and all combinations of individual features represent inventive designs.

BRIEF DESCRIPTION OF THE DRAWINGS

FIG. 1b is a sectional view of another embodiment of FIG. 1a.

DESCRIPTION OF THE PREFERRED EMBODIMENTS

Figure 1:
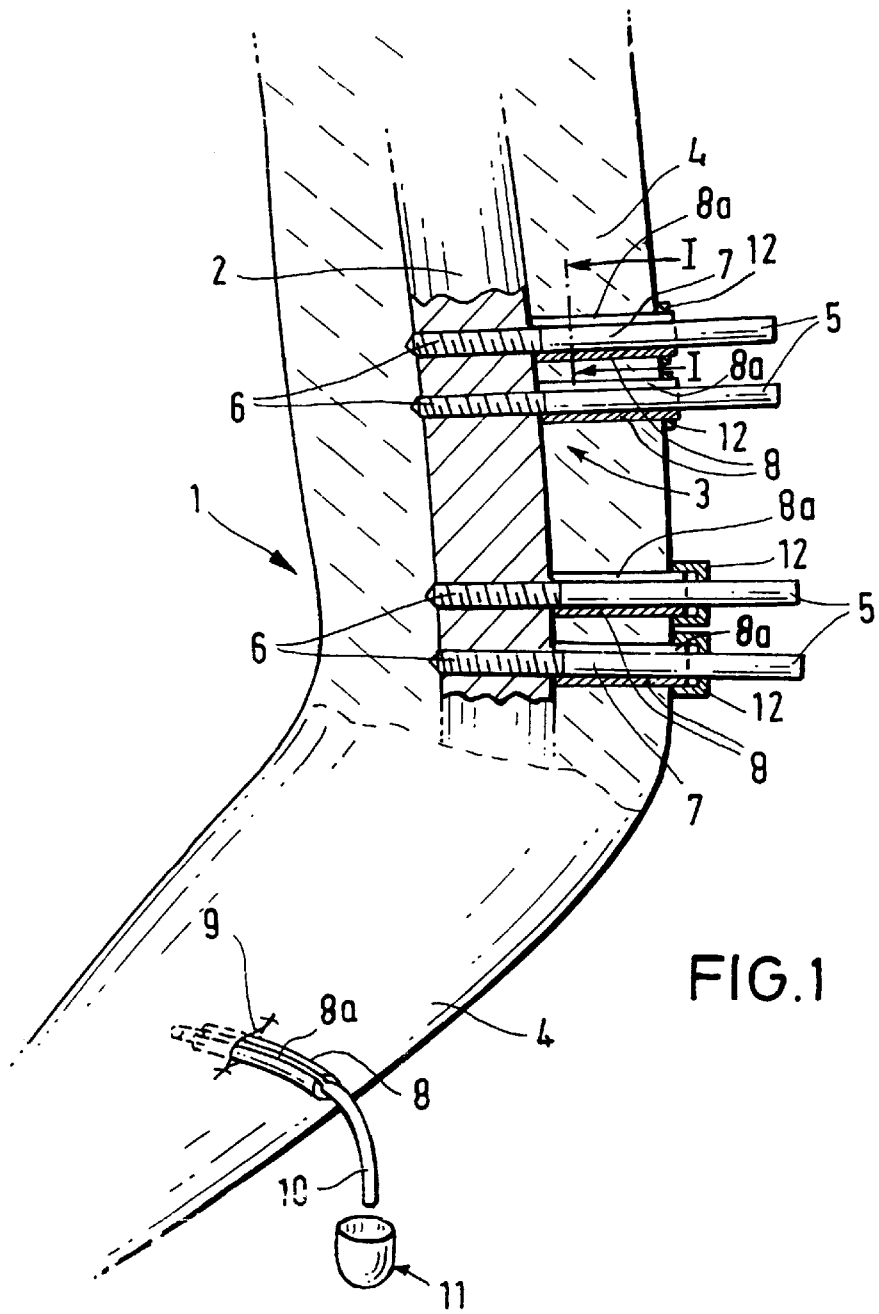
FIG. 1 is a sectional elevation view of the arrangement in accordance with applicant's invention.

FIG. 1 shows an extremity 1 of a human body with an external fixing device 3, only partially represented, that is attached in the region of the end of a bone 2. This device shows in the represented region four fixing screws 5 running through the tissue 4 of the extremity 1 and screwed into the bone 2, with in each case a threaded section 6 located in the region of the bone 2 as well as another, smooth section 7. Put onto the metallic fixing screws 5 in the region of the respective smooth section 7 is the flexible hose 8 showing an antibacterial effect, which hose butts against the bone 2 with one end and juts out from the tissue 4 with the other end, i.e. projects beyond the skin of the extremity 1. Shown on the two upper fixing screws 5 is the implementation form of a ring element 12 in the form of a simple ring of synthetic material that is pushed onto the flexible hose 8 and rests against the skin of the patient. The inner diameter of the ring element 12 is here dimensioned slightly smaller than the outer diameter of the hose 8, so that the ring element 12, by reason of the force fit, fixes the hose 8 axially, especially since the hose 8 is pressed onto the smooth section 7 of the fixing screw 5. The fixing of the hose 8 can also be achieved, for example, through a roughened-up design of the surface of the hose 8 and/or the ring element 12. Shown on the two lower fixing screws 5 is a modified ring element that is formed in the manner of a cap. The ring element 12 is pushed directly onto the smooth section 7 of the screw 5 and with the axial ring section on the outside is slid up onto the hose 8, making contact with the skin of the patient. The illustrated implementation forms with the ring elements find use preferably when the wound is not sewn up, but are also usable in the application cases described below.

Figure 1A:
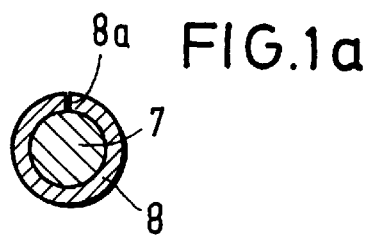
FIG. 1a is a sectional view taken along line I—I in FIG. 1.
Figure 1B:
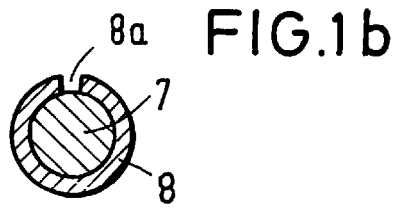

FIG. 1a shows a section according to the line I—I in FIG. 1 through the hose and the smooth section 7, surrounded by this hose, of the fixing screw 5. FIG. 1a illustrates that the hose 8 is provided with a slit 8a that extends over the entire length of the hose 8. The inner diameter of the hose 8 before its being slipped or pushed onto the section 7 of the fixing screw 5 is equal to the outer diameter of the smooth section 7, so that the free longitudinal edges of the hose 8 come into contact with each other, and thus the slit 8a is closed. Such a hose would also be quite applicable for a fixing screw 5 whose smooth section 7 shows a larger diameter. This is shown in FIG. 1b. Consequently, the hose 8 is spread by the smooth section 7, whereby the open gap 8a between the two free longitudinal edges of the hose 8 results. In this case the hose 8 clamps onto the smooth section 7, whereby no further fixing of the hose 8 in the above-described sense is necessary.

The comments on the detail representation according to FIGS. 1a and 1b are valid analogously for the following explanation concerning a modification of the body according to the invention.

FIG. 1 shows in the lower region of the extremity 1 a drainage hose 10 protruding from a sewed-up wound 9, which hose leads to a collection container 11. In the region of the sewed-up wound 9, the flexible, slit hose 8 showing an antibacterial effect surrounds the drainage hose 10, i.e. the flexible hose 8 is inserted into the tissue 4 and partially juts from this on the outside, while on the inside it is lead up to the central wound region. The flexible hose 8 showing an antibacterial effect is held in the wound region through the sewing up of the wound.

In the implementations of the hose 8 shown in FIG. 1, it is pulled as a jacket over existing devices that run through the tissue, for example over the drainage hose shown or the external fixing screw or pin. During the (initial) attachment of the devices, as a rule the possibility exists of pushing the hose 8 in its axial direction onto the orthopedic fixing element, the hose to be surrounded by the hose showing an antibacterial effect, etc. These devices having been attached, it is no longer possible easily to remove the hose showing an antibacterial effect, that is to say, to pull it off in its axial direction and replace it with a new one. However, a radial removal or attachment of the hose is possible by virtue of the continuous slit 8a of the hose 8.

The flexible hose 8 showing an antibacterial effect consists in particular of PVC and preferably is provided with a silver coating over its entire surface.

I claim:

1. A method for draining secretions in medical and surgical procedures comprising the steps of: inserting into a patient's body an antibacterial effective member with a flexible plastic hose protruding partially out of the body and having an antibacterial effective coating and a slit over the entire length of said plastic hose; pushing said flexible plastic hose radially over a drainage hose or an orthopedic fastening element for draining said secretions through said slit and preventing formation of crustings between said plastic hose and said drainage hose.

2. A method for draining secretions in medical and surgical procedures as defined in claim 1, wherein said plastic hose is comprised of polyvinyl chloride.

3. A method for draining secretions in medical and surgical procedures as defined in claim 1, wherein said coating is a silver coating.

4. A method for draining secretions in medical and surgical procedures as defined in claim 1, wherein said coating covers the entire surface of said plastic hose.

5. A method for draining secretions in medical and surgical procedures as defined in claim 1, wherein said plastic hose surrounds said orthopedic fastening element.

6. A method for draining secretions in medical and surgical procedures as defined in claim 1, wherein said fastening element comprises an orthopedic nail.

7. A method for draining secretions in medical and surgical procedures as defined in claim 1, wherein said fastening element comprises an orthopedic screw.

8. A method for draining secretions in medical and surgical procedures as defined in claim 1, wherein said plastic hose surrounds said drainage hose.

9. A method for draining secretions in medical and surgical procedures as defined in claim 7, wherein said plastic hose has an inner diameter equal to or less than an outer diameter of said orthopedic fastening element before being pushed on said fastening element.

10. A method for draining secretions in medical and surgical procedures as defined in claim 1, including the step of pushing a ring-shaped element over said plastic hose and said orthopedic fastening element to hold securely said plastic hose to said orthopedic fastening element.

11. A method for draining secretions in medical and surgical procedures comprising the steps of: inserting into a patient's body an antibacterial effective member with a flexible plastic hose protruding partially out of the body and having an antibacterial effective coating and a slit over the entire length of said plastic hose; pushing said flexible plastic hose radially over a drainage hose or an orthopedic fastening element, said drainage hose or said orthopedic fastening element being substantially surrounded by said plastic hose for draining said secretions through said slit and preventing formation of crustings between said plastic hose and said drainage hose.

12. A method for draining secretions in medical and surgical procedures as defined in claim 11, wherein said plastic hose is comprised of polyvinyl chloride.

13. A method for draining secretions in medical and surgical procedures as defined in claim 11, wherein said coating is a silver coating.

14. A method for draining secretions in medical and surgical procedures as defined in claim 11, wherein said coating covers the entire surface of said plastic hose.

15. A method for draining secretions in medical and surgical procedures as defined in claim 11, wherein said plastic hose surrounds said drainage hose.

16. A method for draining secretions in medical and surgical procedures as defined in claim 11, wherein said plastic hose has an inner diameter equal to or less than an outer diameter of said orthopedic fastening element or said drainage hose before being pushed on said fastening element before being pushed on said fastening element or said drainage hose.

17. A method for draining secretions in medical and surgical procedures as defined in claim 11, including the step of pushing a ring-shaped element over said plastic hose and said orthopedic fastening element to hold securely said plastic hose.

18. A method for draining secretions in medical and surgical procedures comprising the steps of: inserting into a patient's body an antibacterial effective member with a flexible plastic hose protruding partially out of the body and having an antibacterial effective coating and a slit over the entire length of said plastic hose; pushing said flexible plastic hose radially over a drainage hose or an orthopedic fastening element for draining said secretions through said slit and preventing formation of crustings between said plastic hose and said drainage hose; and pushing a ring-shaped element over said plastic hose and said orthopedic fastening element to hold securely said plastic hose to said orthopedic fastening element.

* * * * *